(12) United States Patent
Funk et al.

(10) Patent No.: US 8,362,174 B2
(45) Date of Patent: Jan. 29, 2013

(54) PROCESS FOR PRODUCING WATER-ABSORBING POLYMER PARTICLES

(75) Inventors: Rüdiger Funk, Niedernhausen (DE); Jürgen Schröder, Ludwigshafen (DE); Thomas Pfeiffer, Boehl-Iggelheim (DE); Matthias Weismantel, Jossgrund-Oberndorf (DE); Stefan Blei, Mannheim (DE)

(73) Assignee: BASF SE, Ludwigshafen (DE)

( * ) Notice: Subject to any disclaimer, the term of this patent is extended or adjusted under 35 U.S.C. 154(b) by 93 days.

(21) Appl. No.: 13/031,468

(22) Filed: Feb. 21, 2011

(65) Prior Publication Data

US 2011/0204288 A1    Aug. 25, 2011

Related U.S. Application Data

(60) Provisional application No. 61/307,472, filed on Feb. 24, 2010.

(30) Foreign Application Priority Data

Feb. 24, 2010 (EP) .................................. 10154513

(51) Int. Cl.
- C08F 20/06 (2006.01)
- C08J 3/12 (2006.01)
- C08J 3/24 (2006.01)
- F26B 3/02 (2006.01)

(52) U.S. Cl. .................. 526/317.1; 528/503; 34/659

(58) Field of Classification Search ............... 526/317.1; 528/503; 34/659
See application file for complete search history.

(56) References Cited

U.S. PATENT DOCUMENTS

| 5,668,252 A * | 9/1997 | Yokoi et al. .................. 528/503 |
| 7,960,490 B2 * | 6/2011 | Funk et al. .................. 526/317.1 |
| 2011/0204288 A1 | 8/2011 | Funk et al. |

FOREIGN PATENT DOCUMENTS

| WO | WO-2011104139 A1 | 9/2011 |
| WO | WO-2011104152 A1 | 9/2011 |

OTHER PUBLICATIONS

Buccholz, F., et al. Modern Superabsorbent Polymer Technology, "Commercial Processes for the Manufacture of Superabsorbent Polymers." New York: John Wiley & Sons, Inc., 1998, pp. 71-103 and 89-92.

Moyers, Charles G., et al. (editors), "Psychrometry, Evaporative Cooling, and Solids Drying," *Perry's Chemical Engineers' Handbook*, 7th ed., New York, McGraw-Hill, 1997, p. 12-48.

* cited by examiner

*Primary Examiner* — Vu A Nguyen

(74) *Attorney, Agent, or Firm* — Marshall, Gerstein & Borun LLP

(57) ABSTRACT

A process for producing water-absorbing polymer particles, wherein an aqueous polymer gel is dried in a forced-air belt drier on a circulating conveyor belt and the surface of the conveyor belt has a roughness of at least 0.9 μm.

10 Claims, No Drawings

PROCESS FOR PRODUCING WATER-ABSORBING POLYMER PARTICLES

CROSS-REFERENCE TO RELATED APPLICATIONS

This application claims the benefit of European Patent Application No. 10154513.5, filed Feb. 24, 2010, and U.S. provisional application No. 61/307,472, filed Feb. 24, 2010, incorporated herein by reference in its entirety.

The present invention relates to a process for producing water-absorbing polymer particles, wherein an aqueous polymer gel is dried in a forced-air belt drier on a circulating conveyor belt and the surface of the conveyor belt has a roughness of at least 0.9 μm.

Water-absorbing polymer particles are used to produce diapers, tampons, sanitary napkins and other hygiene articles, but also as water-retaining agents in market gardening. The water-absorbing polymer particles are also referred to as superabsorbents.

The production of water-absorbing polymer particles is described in the monograph "Modern Superabsorbent Polymer Technology", F. L. Buchholz and A. T. Graham, Wiley-VCH, 1998, pages 71 to 103.

The aqueous polymer gels obtained by polymerization are typically dried by means of a forced-air belt drier. A problem here is the shrinkage of the polymer gel on the conveyor belt of the forced-air belt drier. This leads to the effect that the conveyor belt, as drying progresses, is no longer covered with polymer gel over the entire conveyor belt width, and some of the drying air bypasses the conveyor belt unutilized at the edge regions.

To solve this problem, the use of multistage forced-air belt driers is proposed, wherein the material being dried is newly distributed on the next conveyor belt in each case (see also in "Perry's Chemical Engineers' Handbook", 7th edition, McGraw-Hill, pages 12-48).

It was an object of the present invention to provide an improved process for drying aqueous polymer gels by means of a forced-air belt drier.

The object is achieved by a process for producing water-absorbing polymer particles by polymerizing a monomer solution or suspension comprising a) at least one ethylenically unsaturated monomer which bears acid groups and may be at least partly neutralized, b) at least one crosslinker, c) at least one initiator, d) optionally one or more ethylenically unsaturated monomers copolymerizable with the monomers mentioned under a) and e) optionally one or more water-soluble polymers, comprising drying of the resulting aqueous polymer gel in a forced-air belt drier by means of a circulating conveyor belt, grinding, classifying and optional thermal surface postcrosslinking, wherein the surface of the circulating conveyor belt has a roughness $R_z$ of at least 0.9 μm.

The surface of the circulating conveyor belt has a roughness $R_z$ of preferably at least 0.95 μm, more preferably of at least 1 μm, most preferably of at least 2 μm. The roughness $R_z$ is the greatest height of the profile and is described in DIN EN ISO 4287.

The present invention is based on the finding that the shrinkage of the polymer gels during drying can be reduced by the selection of suitable surfaces, without increased crack formation. The cause is probably that the polymer gel to be dried has a temperature above the glass transition temperature $T_G$ during the drying. Above the glass transition temperature $T_G$, polymers are elastomeric and tacky. Owing to their tackiness, the polymer particles are therefore capable of adhering on the surface of the conveyor belt, absorbing the tensile forces which occur, and preventing crack formation. This adhesion on the surface is promoted by a high roughness R.

Forced-air belt driers suitable for the process according to the invention are described. for example, in the monograph "Modern Superabsorbent Polymer Technology", F. L. Buchholz and A. T. Graham, Wiley-VCH, 1998, pages 89 to 92.

It is advantageous in the process according to the invention to use forced-air belt driers with conveyor belts and product-contacting surfaces made from stainless steel. It is possible here for the roughness $R_z$ to be adjusted to the desired value by an appropriate surface treatment, for example by sand-blasting. Sand-blasted steel surfaces have a greater roughness $R_z$ than matt or polished steel surfaces.

Stainless steels typically have a chromium content of 10.5 to 13% by weight. The high chromium content leads to a protective passivation layer of chromium dioxide on the steel surface. Further alloy constituents increase the corrosion resistance and improve the mechanical properties.

Particularly suitable steels are austenitic steels with, for example, at least 0.08% by weight of carbon. The austenitic steels advantageously comprise further alloy constituents, preferably niobium or titanium, in addition to iron, carbon, chromium, nickel and optionally molybdenum.

The preferred stainless steels are steels with materials number 1.43xx or 1.45xx according to DIN EN 10020, where xx may be a natural number from 0 to 99. Particularly preferred materials are the steels with materials numbers 1.4301, 1.4541 and 1.4571, especially steel with materials number 1.4301.

The circulating conveyor belt typically has a multitude of orifices. In a preferred embodiment of the present invention, the circulating conveyor belt has, transverse to the direction of transport, a multitude of slots arranged in offset rows and having a length of preferably 5 to 50 mm, more preferably 10 to 40 mm, most preferably 15 to 30 mm, a width of preferably 0.5 to 5 mm, more preferably 1 to 4 mm, most preferably 1.5 to 3 mm, and a ratio of length to width of preferably 2 to 20, more preferably 5 to 15, most preferably 8 to 12.

The width of the forced-air belt drier is preferably from 1 to 10 m, more preferably from 2 to 7.5 m, most preferably from 3 to 5 m.

The length of the forced-air belt drier is preferably from 10 to 80 m, more preferably from 30 to 60 m, most preferably from 40 to 50 m.

The conveyor belt speed of the forced-air belt drier is preferably from 0.005 to 0.05 m/s, more preferably from 0.01 to 0.35 m/s, most preferably from 0.015 to 0.025 m/s.

The residence time on the forced-air belt drier is preferably from 10 to 120 minutes, more preferably from 20 to 90 minutes, most preferably from 30 to 60 minutes.

The water content of the polymer gel bed in the application zone is preferably from 25 to 90% by weight, more preferably from 35 to 70% by weight, most preferably from 40 to 60% by weight. The mean particle size of the aqueous polymer gel is preferably from 0.1 to 10 mm, more preferably from 0.5 to 5 mm, most preferably from 1 to 2 mm.

The height of the polymer gel bed on the conveyor belt of the forced-air belt drier in the application zone is preferably from 2 to 20 cm, more preferably from 5 to 15 cm, most preferably from 8 to 12 cm.

The gas inlet temperatures of the forced-air belt drier are preferably from 150 to 200° C., more preferably from 160 to 190° C., most preferably from 170 to 180° C.

The gas stream used for drying may comprise water vapor. However, the water vapor content should not exceed a value that corresponds to a dew point of preferably at most 50° C., more preferably at most 40° C., most preferably at most 30° C.

The water content of the polymer gel after the drying on the forced-air belt drier is preferably from 0.5 to 15% by weight, more preferably from 1 to 10% by weight, most preferably from 2 to 8% by weight.

A particularly advantageous drying process is described in WO 2001/100300 A1.

The production of the water-absorbing polymer particles is described in detail hereinafter:

The water-absorbing polymer particles are produced by polymerizing a monomer solution or suspension, and are typically water-insoluble.

The monomers a) are preferably water-soluble, i.e. the solubility in water at 23° C. is typically at least 1 g/100 g of water, preferably at least 5 g/100 g of water, more preferably at least 25 g/100 g of water, most preferably at least 35 g/100 g of water.

Suitable monomers a) are, for example, ethylenically unsaturated carboxylic acids, such as acrylic acid, methacrylic acid and itaconic acid. Particularly preferred monomers are acrylic acid and methacrylic acid. Very particular preference is given to acrylic acid.

Further suitable monomers a) are, for example, ethylenically unsaturated sulfonic acids, such as styrenesulfonic acid and 2-acrylamido-2-methylpropanesulfonic acid (AMPS).

Impurities can have a considerable influence on the polymerization. The raw materials used should therefore have a maximum purity. It is therefore often advantageous to specially purify the monomers a). Suitable purification processes are described, for example, in WO 2002/055469 A1, WO 2003/078378 A1 and WO 2004/035514 A1. A suitable monomer a) is, for example, acrylic acid purified according to WO 2004/035514 A1 and comprising 99.8460% by weight of acrylic acid, 0.0950% by weight of acetic acid, 0.0332% by weight of water, 0.0203% by weight of propionic acid, 0.0001% by weight of furfurals, 0.0001% by weight of maleic anhydride, 0.0003% by weight of diacrylic acid and 0.0050% by weight of hydroquinone monomethyl ether.

The proportion of acrylic acid and/or salts thereof in the total amount of monomers a) is preferably at least 50 mol %, more preferably at least 90 mol %, most preferably at least 95 mol %.

The monomers a) typically comprise polymerization inhibitors, preferably hydroquinone monoethers, as storage stabilizers.

The monomer solution comprises preferably up to 250 ppm by weight, preferably at most 130 ppm by weight, more preferably at most 70 ppm by weight, preferably at least 10 ppm by weight, more preferably at least 30 ppm by weight, especially around 50 ppm by weight, of hydroquinone monoether, based in each case on the unneutralized monomer a). For example, the monomer solution can be prepared by using an ethylenically unsaturated monomer bearing acid groups with an appropriate content of hydroquinone monoether.

Preferred hydroquinone monoethers are hydroquinone monomethyl ether (MEHQ) and/or alpha-tocopherol (vitamin E).

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of the monomer a). In addition, polyvalent metal salts which can form coordinate bonds with at least two acid groups of the monomer a) are also suitable as crosslinkers b).

Crosslinkers b) are preferably compounds having at least two polymerizable groups which can be polymerized free-radically into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 2002/032962 A2.

Preferred crosslinkers b) are pentaerythrityl triallyl ether, tetraallyloxyethane, methylenebismethacrylamide, 15-tuply ethoxylated trimethylolpropane triacrylate, polyethylene glycol diacrylate, trimethylolpropane triacrylate and triallylamine.

Very particularly preferred crosslinkers b) are the polyethoxylated and/or -propoxylated glycerols which have been esterified with acrylic acid or methacrylic acid to give di- or triacrylates, as described, for example, in WO 2003/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol, especially the triacrylate of 3-tuply ethoxylated glycerol.

The amount of crosslinker b) is preferably 0.05 to 1.5% by weight, more preferably 0.1 to 1% by weight and most preferably 0.3 to 0.6% by weight, based in each case on monomer a). With rising crosslinker content, the centrifuge retention capacity (CRC) falls and the absorption under a pressure of 21.0 g/cm$^2$ (AUL0.3 psi) passes through a maximum.

The initiators c) used may be all compounds which generate free radicals under the polymerization conditions, for example thermal initiators, redox initiators, photoinitiators. Suitable redox initiators are sodium peroxodisulfate/ascorbic acid, hydrogen peroxide/ascorbic acid, sodium peroxodisulfate/sodium bisulfite and hydrogen peroxide/sodium bisulfite. Preference is given to using mixtures of thermal initiators and redox initiators, such as sodium peroxodisulfate/hydrogen peroxide/ascorbic acid. The reducing component used is, however, preferably a mixture of the sodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Brüggemann Chemicals; Heilbronn; Germany).

Ethylenically unsaturated monomers d) copolymerizable with the ethylenically unsaturated monomers a) bearing acid groups are, for example, acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, diethylaminoethyl methacrylate.

The water-soluble polymers e) used may be polyvinyl alcohol, polyvinylpyrrolidone, starch, starch derivatives, modified cellulose, such as methylcellulose or hydroxyethylcellulose, gelatin, polyglycols or polyacrylic acids, preferably starch, starch derivatives and modified cellulose.

Typically, an aqueous monomer solution is used. The water content of the monomer solution is preferably from 40 to 75% by weight, more preferably from 45 to 70% by weight and most preferably from 50 to 65% by weight. It is also possible to use monomer suspensions, i.e. monomer solutions with excess monomer a), for example sodium acrylate. With rising water content, the energy requirement in the subsequent drying rises, and, with falling water content, the heat of polymerization can only be removed inadequately.

For optimal action, the preferred polymerization inhibitors require dissolved oxygen. The monomer solution can therefore be freed of dissolved oxygen before the polymerization by inertization, i.e. flowing an inert gas through, preferably nitrogen or carbon dioxide. The oxygen content of the monomer solution is preferably lowered before the polymerization to less than 1 ppm by weight, more preferably to less than 0.5 ppm by weight, most preferably to less than 0.1 ppm by weight.

Suitable reactors are, for example, kneading reactors or belt reactors. In the kneader, the aqueous polymer gel formed in the polymerization of an aqueous monomer solution or suspension is comminuted continuously by, for example, contrarotatory stirrer shafts, as described in WO 2001/038402 A1. Polymerization on the belt is described, for example, in DE 38 25 366 A1 and U.S. Pat. No. 6,241,928. Polymerization in a belt reactor forms an aqueous polymer gel which has to be comminuted in a further process step, for example in an extruder or kneader.

To improve the drying properties, the comminuted aqueous polymer gel obtained by means of a kneader can additionally be extruded.

The acid groups of the resulting aqueous polymer gels have typically been partially neutralized. Neutralization is preferably carried out at the monomer stage. This is typically accomplished by mixing in the neutralizing agent as an aqueous solution or preferably also as a solid. The degree of neutralization is preferably from 25 to 95 mol %, more preferably from 30 to 80 mol % and most preferably from 40 to 75 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts. Particularly preferred alkali metals are sodium and potassium, but very particular preference is given to sodium hydroxide, sodium carbonate or sodium hydrogencarbonate and also mixtures thereof.

However, it is also possible to carry out neutralization after the polymerization, at the stage of the aqueous polymer gel formed in the polymerization. It is also possible to neutralize up to 40 mol %, preferably from 10 to 30 mol % and more preferably from 15 to 25 mol % of the acid groups before the polymerization by adding a portion of the neutralizing agent actually to the monomer solution and setting the desired final degree of neutralization only after the polymerization, at the aqueous polymer gel stage. When the aqueous polymer gel is neutralized at least partly after the polymerization, the aqueous polymer gel is preferably comminuted mechanically, for example by means of an extruder, in which case the neutralizing agent can be sprayed, sprinkled or poured on and then carefully mixed in. To this end, the gel mass obtained can be repeatedly extruded for homogenization.

The aqueous polymer gel is then dried with a forced-air belt drier until the residual moisture content is preferably 0.5 to 15% by weight, more preferably 1 to 10% by weight and most preferably 2 to 8% by weight, the residual moisture content being determined by EDANA recommended test method No. WSP 230.2-05 "Moisture Content". In the case of too high a residual moisture content, the dried polymer gel has too low a glass transition temperature $T_g$ and can be processed further only with difficulty. In the case of too low a residual moisture content, the dried polymer gel is too brittle and, in the subsequent comminution steps, undesirably large amounts of polymer particles with an excessively low particle size are obtained ("fines"). The solids content of the gel before the drying is preferably from 25 to 90% by weight, more preferably from 35 to 70% by weight and most preferably from 40 to 60% by weight.

Thereafter, the dried polymer gel is ground and classified, and the apparatus used for grinding may typically be single- or multistage roll mills, preferably two- or three-stage roll mills, pin mills, hammer mills or vibratory mills.

The mean particle size of the polymer particles removed as the product fraction is preferably at least 200 μm, more preferably from 250 to 600 μm and very particularly from 300 to 500 μm. The mean particle size of the product fraction may be determined by means of EDANA recommended test method No. WSP 220.2-05 "Particle Size Distribution", where the proportions by mass of the screen fractions are plotted in cumulated form and the mean particle size is determined graphically. The mean particle size here is the value of the mesh size which gives rise to a cumulative 50% by weight.

The proportion of particles with a particle size of at least 150 μm is preferably at least 90% by weight, more preferably at least 95% by weight, most preferably at least 98% by weight.

Polymer particles with too small a particle size lower the permeability (SFC). The proportion of excessively small polymer particles ("fines") should therefore be small.

Excessively small polymer particles are therefore typically removed and recycled into the process. This is preferably done before, during or immediately after the polymerization, i.e. before the drying of the aqueous polymer gel. The excessively small polymer particles can be moistened with water and/or aqueous surfactant before or during the recycling.

It is also possible to remove excessively small polymer particles in later process steps, for example after the surface postcrosslinking or another coating step. In this case, the excessively small polymer particles recycled are surface postcrosslinked or coated in another way, for example with fumed silica.

When a kneading reactor is used for polymerization, the excessively small polymer particles are preferably added during the last third of the polymerization.

When the excessively small polymer particles are added at a very early stage, for example actually to the monomer solution, this lowers the centrifuge retention capacity (CRC) of the resulting water-absorbing polymer particles. However, this can be compensated, for example, by adjusting the amount of crosslinker b) used.

When the excessively small polymer particles are added at a very late stage, for example not until an apparatus connected downstream of the polymerization reactor, for example an extruder, the excessively small polymer particles can be incorporated into the resulting aqueous polymer gel only with difficulty. Insufficiently incorporated, excessively small polymer particles are, however, detached again from the dried polymer gel during the grinding, are therefore removed again in the course of classification and increase the amount of excessively small polymer particles to be recycled.

The proportion of particles having a particle size of at most 850 μm is preferably at least 90% by weight, more preferably at least 95% by weight, most preferably at least 98% by weight.

The proportion of particles having a particle size of at most 600 μm is preferably at least 90% by weight, more preferably at least 95% by weight, most preferably at least 98% by weight.

Polymer particles with too great a particle size lower the swell rate. The proportion of excessively large polymer particles should therefore likewise be small.

Excessively large polymer particles are therefore typically removed and recycled into the grinding of the dried polymer gel.

To further improve the properties, the polymer particles may be surface postcrosslinked. Suitable surface postcrosslinkers are compounds which comprise groups which can form covalent bonds with at least two carboxylate groups of the polymer particles. Suitable compounds are, for example, polyfunctional amines, polyfunctional amido amines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617 A1 and EP 0 450 922 A2, or β-hydroxyalkylamides, as described in DE 102 04 938 A1 and U.S. Pat. No. 6,239,230.

Additionally described as suitable surface postcrosslinkers are cyclic carbonates in DE 40 20 780 C1, 2-oxazolidinone and derivatives thereof, such as 2-hydroxyethyl-2-oxazolidinone, in DE 198 07 502 A1, bis- and poly-2-oxazolidinones in DE 198 07 992 C1, 2-oxotetrahydro-1,3-oxazine and derivatives thereof in DE 198 54 573 A1, N-acyl-2-oxazolidinones in DE 198 54 574 A1, cyclic ureas in DE 102 04 937 A1, bicyclic amido acetals in DE 103 34 584 A1, oxetanes and cyclic ureas in EP 1 199 327 A2 and morpholine-2,3-dione and derivatives thereof in WO 2003/031482 A1.

Preferred surface postcrosslinkers are ethylene carbonate, ethylene glycol diglycidyl ether, reaction products of polyamides with epichlorohydrin and mixtures of propylene glycol and 1,4-butanediol.

Very particularly preferred surface postcrosslinkers are 2-hydroxyethyl-2-oxazolidinone, 2-oxazolidinone and 1,3-propanediol.

In addition, it is also possible to use surface postcrosslinkers which comprise additional polymerizable ethylenically unsaturated groups, as described in DE 37 13 601 A1.

The amount of surface postcrosslinker is preferably 0.001 to 2% by weight, more preferably 0.02 to 1% by weight and most preferably 0.05 to 0.2% by weight, based in each case on the polymer particles.

In a preferred embodiment of the present invention, polyvalent cations are applied to the particle surface in addition to the surface postcrosslinkers before, during or after the surface postcrosslinking.

The polyvalent cations usable in the process according to the invention are, for example, divalent cations such as the cations of zinc, magnesium, calcium, iron and strontium, trivalent cations such as the cations of aluminum, iron, chromium, rare earths and manganese, tetravalent cations such as the cations of titanium and zirconium. Possible counterions are chloride, bromide, sulfate, hydrogensulfate, carbonate, hydrogencarbonate, nitrate, phosphate, hydrogenphosphate, dihydrogenphosphate and carboxylate, such as acetate, citrate and lactate. Aluminum sulfate and aluminum lactate are preferred. Apart from metal salts, it is also possible to use polyamines as polyvalent cations.

The amount of polyvalent cation used is, for example, 0.001 to 1.5% by weight, preferably 0.005 to 1% by weight and more preferably 0.02 to 0.8% by weight, based in each case on the polymer particles.

The surface postcrosslinking is typically performed in such a way that a solution of the surface postcrosslinker is sprayed onto the dried polymer particles. After the spraying, the polymer particles coated with surface postcrosslinker are dried thermally, and the surface postcrosslinking reaction can take place either during or after the drying.

The spraying of a solution of the surface postcrosslinker is preferably performed in mixers with moving mixing tools, such as screw mixers, disk mixers and paddle mixers. Particular preference is given to horizontal mixers such as paddle mixers, very particular preference to vertical mixers. The distinction between horizontal mixers and vertical mixers is made by the position of the mixing shaft, i.e. horizontal mixers have a horizontally mounted mixing shaft and vertical mixers a vertically mounted mixing shaft. Suitable mixers are, for example, horizontal Pflugschar® plowshare mixers (Gebr. Lödige Maschinenbau GmbH; Paderborn; Germany), Vrieco-Nauta continuous mixers (Hosokawa Micron BV; Doetinchem; the Netherlands), Processall Mixmill mixers (Processall Incorporated; Cincinnati; US) and Schugi Flexomix® (Hosokawa Micron BV; Doetinchem; the Netherlands). However, it is also possible to spray on the surface postcrosslinker solution in a fluidized bed.

The surface postcrosslinkers are typically used in the form of an aqueous solution. The penetration depth of the surface postcrosslinker into the polymer particles can be adjusted via the content of nonaqueous solvent and total amount of solvent.

When exclusively water is used as the solvent, a surfactant is advantageously added. This improves the wetting behavior and reduces the tendency to form lumps. However, preference is given to using solvent mixtures, for example isopropanol/water, 1,3-propanediol/water and propylene glycol/water, where the mixing ratio in terms of mass is preferably from 20:80 to 40:60.

The temperature of the water-absorbing polymer particles in the drier is preferably from 100 to 250° C., more preferably from 130 to 220° C., most preferably from 150 to 200° C. The residence time in the drier is preferably from 10 to 120 minutes, more preferably from 10 to 90 minutes, most preferably from 30 to 60 minutes. The fill level of the drier is preferably from 30 to 80%, more preferably from 40 to 75%, most preferably from 50 to 70%. The fill level of the drier can be adjusted via the height of the overflow weir.

Subsequently, the surface postcrosslinked polymer particles can be classified again, excessively small and/or excessively large polymer particles being removed and recycled into the process.

To further improve the properties, the surface postcrosslinked polymer particles can be coated or remoisturized.

The remoisturizing is preferably performed at 30 to 80° C., more preferably at 35 to 70° C., most preferably at 40 to 60° C. At excessively low temperatures, the water-absorbing polymer particles tend to form lumps, and, at higher temperatures, water already evaporates to a noticeable degree. The amount of water used for remoisturizing is preferably from 1 to 10% by weight, more preferably from 2 to 8% by weight and most preferably from 3 to 5% by weight. The remoisturizing increases the mechanical stability of the polymer particles and reduces their tendency to static charging.

Suitable coatings for improving the swell rate and the permeability (SFC) are, for example, inorganic inert substances, such as water-insoluble metal salts, organic polymers, cationic polymers and di- or polyvalent metal cations. Suitable coatings for dust binding are, for example, polyols. Suitable coatings for counteracting the undesired caking tendency of the polymer particles are, for example, fumed silica, such as Aerosil® 200, and surfactants, such as Span® 20.

The water-absorbing polymer particles produced by the process according to the invention have a moisture content of preferably 0 to 15% by weight, more preferably 0.2 to 10% by weight and most preferably 0.5 to 8% by weight, the moisture content being determined by EDANA recommended test method No. WSP 230.2-05 "Moisture Content".

The water-absorbing polymer particles produced by the process according to the invention have a centrifuge retention capacity (CRC) of typically at least 15 g/g, preferably at least 20 g/g, more preferably at least 22 g/g, especially preferably at least 24 g/g and most preferably at least 26 g/g. The centrifuge retention capacity (CRC) of the water-absorbing polymer particles is typically less than 60 g/g. The centrifuge retention capacity (CRC) is determined by EDANA recommended test method No. WSP 241.2-05 "Centrifuge Retention Capacity".

EXAMPLES

Example 1

Production of the Aqueous Polymer Gel 4485 g of a 37.3% by weight aqueous sodium acrylate solution were mixed with 427 g of acrylic acid and 1024 g of water, and inertized with nitrogen. This mixture was introduced into a nitrogen-inertized Werner & Pfleiderer LUK 8,0 K2 kneader (2 sigma shafts), and admixed successively with 11.96 g of 15-tuply ethoxylated trimethylolpropane triacrylate, 20.50 g of a 0.5% by weight aqueous ascorbic acid solution and 31.66 g of a 15% by weight aqueous sodium persulfate solution. The kneader was stirred at maximum speed (approx. 98 rpm of the faster shaft, approx. 49 rpm of the slower shaft, ratio approx. 2:1). Immediately after the addition of sodium persulfate, the kneader jacket was heated with heat carrier at 74° C. On attainment of the maximum temperature, the jacket heating was switched off and the mixture was allowed to react in the kneader for a further 15 minutes. The resulting polymer gel was cooled to 63° C., emptied out and used for the subsequent tests.

Example 2

Comparative Example 1234 g of aqueous polymer gel from example 1 were introduced into a drying tray and dried at 175° C. in a forced-air drying cabinet for 370 minutes. The drying tray consisted of a stainless steel frame of height 5 cm with internal dimensions of 23.7×23.7 cm and an exchangeable stainless steel base plate (materials number 1.4301). The stainless steel base plate was square, had parallel rows of slots with an opening of 2×20 mm and fitted exactly into the stainless steel frame.

The surface of the stainless steel base plate had a roughness $R_z$ of 0.32 µm.

The stainless steel frame was sprayed beforehand with PTFE spray in order to prevent any possible adhesion. Before the drying stage, the aqueous polymer gel in the drying tray was weighted down with a fitting stainless steel plate, in order to prevent the edges of the polymer gel from curving upward in the course of drying. The stainless steel plate had parallel rows of slots with an opening of 2×20 mm.

The polymer gel shrunk three-dimensionally in the course of drying. For the evaluation of the shrinkage, only the two-dimensional or areal shrinkage was determined. For this purpose, the dried polymer gel was placed as a complete block onto a black substrate and photographed from above at a distance of 56 cm, and the percentage shrinkage was recorded via a pixel evaluation.

In order to rule out aging processes of the polymer gel and other disruptive parameters, a parallel drying was carried out with a stainless steel base plate with a roughness $R_z$ of 1.03 µm and the shrinkage of this control measurement was equated to 100%.

The shrinkage of the stainless steel base plate with a roughness $R_z$ of 0.32 µm examined was 95%. The dried polymer gel was removable from the stainless steel base plate only with very great difficulty.

Example 3

Comparative Example

The procedure was as in example 2. The stainless steel base plate was exchanged.

The surface of the stainless steel base plate had a roughness $R_z$ of 0.87 µm.

The shrinkage of the stainless steel base plate with a roughness $R_z$ of 0.87 µm examined was 152%. The dried polymer gel was removable easily from the stainless steel base plate.

Example 4

The procedure was as in example 2. The stainless steel base plate was exchanged.

The surface of the stainless steel base plate had a roughness $R_z$ of 7.32 µm.

The shrinkage of the stainless steel base plate with a roughness $R_z$ of 7.32 µm examined was 92%. The dried polymer gel was removable readily from the stainless steel base plate.

Example 5

The procedure was as in example 2. The stainless steel base plate was exchanged.

The surface of the stainless steel base plate had a roughness $R_z$ of 18.4 µm.

The shrinkage of the stainless steel base plate with a roughness $R_z$ of 18.4 µm examined was 67%. The dried polymer gel was removable readily from the stainless steel base plate.

The invention claimed is:

1. A process for producing water-absorbing, polymer particles by polymerizing an aqueous monomer solution or suspension comprising
   a) at least one ethylenically unsaturated monomer which bears an acid group and may be at least partly neutralized,
   b) at least one crosslinker,
   c) at least one initiator,
   d) optionally one or more ethylenically unsaturated monomer copolymerizable with the monomer mentioned under a) and
   e) optionally one or more water-soluble polymer, and drying the resulting aqueous polymer gel in a forced-air belt dryer by means of a circulating conveyor belt, grinding, classifying, and optional thermal surface postcrosslinking, wherein the surface of the circulating conveyor belt has a roughness $R_z$ of at least 0.9 µm.

2. The process according to claim 1, wherein the circulating conveyor belt is made from austenitic steel.

3. The process according to claim 1, wherein the circulating conveyor belt has a multitude of orifices.

4. The process according to claim 1, wherein the circulating conveyor belt has, transverse to the direction of transport, a multitude of slots arranged in offset rows and having a length of 5 to 50 mm, a width of 0.5 to 5 mm and a ratio of length to width of 2 to 20.

5. The process according to claim 1, wherein the circulating conveyor belt has a width of at least 1 m.

6. The process according to claim 1, wherein a conveyor belt speed is from 0.005 to 0.05 m/s.

7. The process according to claim 1, wherein a water content of the polymer gel before drying in the forced-air belt dryer is from 30 to 70% by weight.

8. The process according to claim 1, wherein a water content of the polymer gel after the drying in the forced-air belt dryer is from 0.5 to 15% by weight.

9. The process according to claim 1, wherein a height of the polymer gel bed on the circulating conveyor belt is from 2 to 20 cm.

10. The process according to claim 1, wherein the water-absorbing polymer particles have a centrifuge retention capacity of at least 15 g/g.

* * * * *